United States Patent
Schüβler et al.

(10) Patent No.: US 9,561,120 B2
(45) Date of Patent: Feb. 7, 2017

(54) INTRAVASCULAR FUNCTIONAL ELEMENT AND METHOD OF MANUFACTURE

(71) Applicant: Admedes Inc, Livermore, CA (US)

(72) Inventors: Andreas Schüβler, Pforzheim (DE); Gerd Siekmeyer, Karlsruhe (DE); Giorgio Cattaneo, Karlsruhe (DE); Werner Mailänder, Engelsbrand Grunbach (DE)

(73) Assignee: ADMEDES INC., Livermore, CA (US)

( * ) Notice: Subject to any disclaimer, the term of this patent is extended or adjusted under 35 U.S.C. 154(b) by 0 days.

(21) Appl. No.: 14/177,470

(22) Filed: Feb. 11, 2014

(65) Prior Publication Data

US 2014/0228934 A1    Aug. 14, 2014

(30) Foreign Application Priority Data

Feb. 11, 2013    (DE) .................. 10 2013 101 334

(51) Int. Cl.
*A61F 2/86* (2013.01)
*A61F 2/88* (2006.01)
(Continued)

(52) U.S. Cl.
CPC .  *A61F 2/86* (2013.01); *A61F 2/88* (2013.01); *A61L 31/022* (2013.01); *A61L 31/14* (2013.01);
(Continued)

(58) Field of Classification Search
CPC ...... A61L 31/022; A61L 31/16; A61L 31/082; A61L 2300/61; A61L 31/088; A61L 2300/602; A61L 2420/08; A61L 29/10; A61L 29/16; A61L 2300/41; A61L 2300/416; A61L 2300/42; A61L 2300/604; A61L 2300/608; A61L 2300/62;A61F 2/91; A61F 2/0077; A61F 2/86; A61F 2/88; A61F 2/90; A61F 2/915; A61F 2002/30107; A61F 2002/91533; A61F 2002/91541; A61F 2210/0009; A61F 2210/0014; A61F 2210/0076; A61F 2230/005; A61F 2230/0054; A61F 2250/0098
See application file for complete search history.

(56) References Cited

U.S. PATENT DOCUMENTS 3,643,658 A     2/1972  Steinemenan
5,354,623 A  *  10/1994 Hall .................... B23K 35/004
                                                     228/207
(Continued)

FOREIGN PATENT DOCUMENTS

CH          497891       10/1970
DE         19506188       8/1996
(Continued)

OTHER PUBLICATIONS

Oxford Dictionary, Definition of coil, retrieved on Jan. 21, 2015.*
(Continued)

*Primary Examiner* — Christian Sevilla
*Assistant Examiner* — Seema Mathew
(74) *Attorney, Agent, or Firm* — Hassan Abbas Shakir; Katten Muchin Rosenman LLP

(57) ABSTRACT

The invention relates to a method of manufacture of an intravascular functional element that can be introduced into a hollow organ and that comprises at least one wire (10) of an alloy having nickel and titanium as alloying elements, with the following steps: preparation of a metal body of the wire (10) with a metallic surface, then formation of a first oxide layer on the metallic surface of the metal body, then performance of a heat treatment of the wire (10) in a nitrogen-containing salt bath for thermal formation of a second mixed oxide layer on the first oxide layer, wherein (Continued)

the total layer thickness is 15 nm to 100 nm and the mixed oxide layer contains $TiO_2$ and at least one nitride, especially titanium oxynitride and/or titanium nitride.

27 Claims, 7 Drawing Sheets

(51) Int. Cl.
  *C23C 8/02* (2006.01)
  *C23C 8/52* (2006.01)
  *A61L 31/02* (2006.01)
  *A61L 31/14* (2006.01)
  *A61F 2/90* (2013.01)

(52) U.S. Cl.
  CPC . *C23C 8/02* (2013.01); *C23C 8/52* (2013.01); *A61F 2/90* (2013.01); *A61L 2400/18* (2013.01)

(56) References Cited

U.S. PATENT DOCUMENTS

| | | | |
|---|---|---|---|
| 6,110,204 A | 8/2000 | Lazarov | |
| 6,287,315 B1* | 9/2001 | Wijeratne | A61M 25/10184 606/108 |
| 6,402,859 B1* | 6/2002 | Ishii | A61L 29/02 148/421 |
| 7,497,443 B1* | 3/2009 | Steinetz | F16J 15/0887 277/644 |
| 8,639,352 B2* | 1/2014 | Wang | A61N 1/05 174/102 R |
| 9,409,008 B2* | 8/2016 | Li | A61N 1/05 |
| 2003/0153971 A1* | 8/2003 | Chandrasekaran | A61F 2/07 623/1.15 |
| 2004/0117001 A1 | 6/2004 | Pelton et al. | |
| 2005/0131520 A1 | 6/2005 | Zilla | |
| 2005/0191408 A1* | 9/2005 | Aharonov | A61L 27/045 427/2.27 |
| 2006/0157159 A1 | 7/2006 | Yeung | |
| 2006/0276875 A1 | 12/2006 | Stinson | |
| 2008/0195196 A1 | 8/2008 | Asgari | |
| 2009/0076588 A1 | 3/2009 | Weber | |
| 2009/0264975 A1* | 10/2009 | Flanagan et al. | 623/1.2 |
| 2010/0030319 A1* | 2/2010 | Weber | A61F 2/88 623/1.11 |
| 2010/0076543 A1* | 3/2010 | Melsheimer | A61F 2/07 623/1.13 |
| 2010/0185271 A1 | 7/2010 | Zhang | |
| 2011/0166640 A1 | 7/2011 | Leewood | |
| 2014/0238722 A1* | 8/2014 | Hayashishita | H01B 13/34 174/115 |
| 2016/0022427 A1* | 1/2016 | Nakagawa | A61F 2/44 623/23.47 |

FOREIGN PATENT DOCUMENTS

| | | |
|---|---|---|
| DE | 60310686 | 4/2007 |
| EP | 1522605 | 4/2005 |

OTHER PUBLICATIONS

German Office Action dated Sep. 3, 2013 for the Corresponding German Patent Application No. DE 10 2013 101 334.1.

European Search Report dated Jul. 11, 2014 for the Corresponding European Patent Application No. EP 14154280.3.

C. Trepanier, et al., "Effect of medication of oxide layer on NiTistent corrosion resistance"; Journal of Biomedical Materials Research, Bd. 43, Nr. 4; Dec. 1, 1998; pp. 433-440.

Neelakantan L et al, "Selective surface oxidation and nitridation of NiTi shape memory alloys by reduction annealing"; Corrosion Science, Oxford, GB, Bd. 51, Nr. 3; Mar. 1, 2009;pp. 635-641.

Y. Cheng et al, "Surface characterization and mechanical property of TiN/Ti-coated NiTi alloy by PIIID"; Surface and Coatings Technology, Bd. 201, Nr. 15; Aug. 27, 2006; pp. 6869-6873.

Office Action dated Sep. 19, 2013 in applicants German patent application DE 10 2013 101 337.6.

File history of applicant's U.S. Appl. No. 14/177,471 retrieved Jun. 1, 2016.

* cited by examiner

Untreated Comparison Sample

Wire Manufactured According to the Invention

INTRAVASCULAR FUNCTIONAL ELEMENT AND METHOD OF MANUFACTURE

CROSS-REFERENCE TO RELATED APPLICATIONS

This application claims priority to German patent application DE 10 2013 101 334.1 filed on Feb. 11, 2013 and which is hereby incorporated by reference in its entirety for all purposes.

BACKGROUND OF THE INVENTION

Field of the Invention

The invention relates to a method of manufacture of a functional element, especially a stent, as well as to the use of a salt bath for heat treatment of an intravascular functional element. The invention also relates to an intravascular functional element, especially a stent.

Discussion of the Background of the Invention

In medical technology, stents are usually produced by laser methods. However, braids of Nitinol wires are also used for implants (e.g. stents or occluders). In contrast to stents produced by laser methods, the wires of wire braids slide over one another and therefore permit good shape adaptation of the stent structures. In principle, (vascular) implants may be manufactured from semifinished materials such as sheet, precision tubes or wires.

For example, US 2004/0117001 A1 describes a method of manufacture of a stent from Nitinol. One objective of US 2004/0117001 A1 consists in reducing the nickel content in a near-surface layer in order to prevent nickel from being released from the layer, since thereby the biocompatibility of the stent is impaired. A laser method is proposed for production of the stent. After a cold-working step, the stent is heat-treated and then electropolished at temperatures below 20° C. For thermal oxidation, the stent is exposed to superheated steam at a temperature of 150° C. for 12 h. Thereby an oxidic surface with an Ni content of less than 2 wt % in a layer depth of 10 nm is supposedly obtainable.

The known method has the disadvantage that the oxide layer that can be produced therewith on implants consisting of wire braids wears rapidly. For braids, it is important that the contact surfaces of the wires touching one another have low friction, precisely considering that the implanted braids are continuously exposed to pulsatile vessel movements and the wires therefore move relative to one another. Above and beyond this, a low coefficient of friction of the wire surfaces is important for good mobility of the implant in an introducing catheter.

One object of the invention is to propose a method with which an intravascular functional element, especially a stent or intravascular coil or intravascular occlusion device can be produced with improved wear and friction properties and good biocompatibility. Another object of the invention is to provide an intravascular functional element, especially a stent or intravascular coil or intravascular occlusion device with improved wear and friction properties and good biocompatibility. A further object of the invention is to propose the use of a salt bath for heat treatment of an intravascular functional element.

SUMMARY OF THE INVENTION

This object is achieved with respect to the method by the subject matter of the present invention, with respect to the use by the subject matter of the present invention and with respect to the functional element by the subject matter of the present invention.

In particular, the object is achieved by a method of manufacture of an intravascular functional element that can be introduced into a hollow organ and that comprises at least one wire of an alloy having nickel and titanium as alloying elements. In the method, a metal body of the wire is prepared with a metallic surface. Then a first oxide layer is formed on the metallic surface of the metal body. For thermal formation of a second mixed oxide layer on the first oxide layer, a heat treatment of the wire is carried out in a nitrogen-containing salt bath, wherein the total layer thickness is 15 nm to 100 nm and the mixed oxide layer contains $TiO_2$ and at least one nitride, especially titanium oxynitride and/or titanium nitride.

For preparation of the wire metal body with a metallic surface, a pretreatment is carried out in which an oxide layer usually present on the wire surface is removed. This oxide layer, with a thickness of 0.2 µm to 5 µm, is formed during wire manufacture, when a heat treatment is applied to adjust the material characteristics of the wire. Various methods, which may be used within the scope of the invention, come into question for removal of the oxide layer, in order to prepare a wire metal body with a metallic surface. The invention is not limited to these methods.

In a preferred embodiment, the above manufacturing-related oxide layer is removed by electropolishing. In this process, metal together with impurities as well as an oxide layer formed naturally on the wire surface is stripped from the wire surface in a way known in itself in an electrolyte bath under the action of current, so that a smooth and homogeneous metallic surface that is substantially oxide-free is obtained after electropolishing.

The wire metal body with a metallic surface may be produced in other ways, for example by chemical or electrochemical or mechanical stripping of the surface layer of the wire. One option for chemical stripping is etching or pickling. In this way the natural oxide layer is removed, exposing the metallic surface of the wire body. The process parameters used for this purpose are known to the person skilled in the art, for example from US 2004/0117001 A1. Microabrasive stripping methods, which may likewise be used in the invention, are also known.

A first oxide layer, on which the second mixed oxide layer is thermally applied, is formed on the metallic surface of the wire metal body. In the simplest case, the formation of the first oxide layer can take place in the form of a natural oxide layer, which is formed when the metallic surface of the wire metal body is exposed to the ambient air. If the pretreatment of the wire is carried out by electropolishing, for example, it has been found that the natural first oxide layer has a thickness of approximately 3 nm to 10 nm.

The wire cross section is not limited to any particular shape. The cross-sectional shape of the wire may be round, especially circular or elliptical, or polygonal or other shape.

The invention has several advantages.

The oxide layer formed on the wire surface is low in nickel and contains $TiO_2$, whereby the corrosion behavior and the biocompatibility of the implant are improved. The formation of the oxide layer as a mixed oxide layer, in which at least one nitride is present, especially titanium nitride and/or titanium oxynitride, increases the layer hardness, whereby the wear of the functional element, especially of the implant, is reduced when it is subjected to stress in the vessel. This advantage is noticeable in particular for braids, such as braided stents, in which wires touch and slide over one another. In this way the quality of the functional element, especially of the implant, is improved, for example in terms of compliance in the vessel. Above and beyond this, the coefficient of friction of the surface of the functional element, especially of the implant, is improved, leading to better sliding behavior in the catheter. The good sliding properties act on the one hand between the wires themselves, whereby the crimpability, i.e. the ability of the functional element to be compressed, is improved. On the other hand, the good sliding properties act between the wires and the inside wall of the catheter. The resulting reduced pushing force necessary to move the functional element, especially an implant, in the catheter increases the safety, since the risk of blockage and of damage to the functional element, especially an implant, in the catheter is reduced. The same is true for introducer systems, in which introduction of the functional element is achieved not by movement of the functional element itself but instead by a relative movement between part of the introducer system and the functional element.

The layer thickness of 10 nm to 100 nm has the advantage that the wear resistance is improved compared with a wire that has been merely electropolished. The natural oxide layer, which is formed, for example, after electropolishing, has a layer thickness of approximately 3 to 10 nm, which is why the layer can be easily rubbed off. The layer thickness increased according to the invention, together with the nitriding of the oxide layer, improves the abrasion resistance.

Compared with conventional oxide layers that form with a thickness of more than 200 nm on NiTi wires during wire manufacture, the inventive mixed oxide layer is more protective against the escape of nickel ions, as is demonstrated, for example, by the good corrosion behavior of the layer. The invention therefore unites the good protective properties of a very thin oxide layer with the good abrasion resistance of a relatively thick layer as well as with good sliding properties.

Advantageously the total layer thickness, i.e. the thickness of the first and second layers, is at least 30 nm, especially at least 35 nm, especially at least 40 nm, especially at least 45 nm, especially at least 50 nm, especially at least 55 nm. The abrasion resistance is further improved with the increase of the lower limit of the layer-thickness range.

When the total layer thickness is at most 95 nm, especially at most 90 nm, especially at most 85 nm, especially at most 80 nm, especially at most 75 nm, especially at most 70 nm, especially at most 65 nm, especially at most 60 nm, the protective properties of the layer are improved by the reduction of the upper limit of the layer thickness range. Moreover, the risk is less that layer components will be dissolved from the wire surface or that the layer will become brittle—especially during deformations of the wires.

The values cited in the foregoing for the lower limit and the upper limit may be combined respectively with one another, in order to achieve a selective improvement of the respective layer properties. For example, the lower limit for the above maximum values may be 30 nm. A particularly advantageous range of the layer thickness is from 20 nm to 90 nm, especially from 30 nm to 90 nm, especially from 40 nm to 80 nm, especially from 50 nm to 70 nm.

In a preferred embodiment, the peak of the oxygen concentration in the mixed oxide layer forms a plateau. For example, the plateau may be formed in a layer depth of 5 nm to 50 nm, especially from 10 nm to 40 nm, especially from 15 nm to 30 nm. In this case the total layer thickness is at least approximately 60 nm. As a reason for the plateau, it is assumed that the oxygen combines preferentially with nitrogen outwardly toward the layer surface and with titanium inwardly toward the wire material.

The ratio of intensities between nitrogen and oxygen (N/O) is at most 1:2.0, especially from 1:2.5 to 1:10 in the region of the oxygen plateau, and decreases toward the wire metal body, the intensities being determined respectively by Auger electron spectroscopy (AES) in the depth profile through the mixed oxide layer. At the layer surface, the ratio of intensities between nitrogen and oxygen (N/O) is at most approximately 1:2.0, especially approximately 1:2.5. The ratio of 1:2.0 lies in the immediate boundary layer of the layer surface (approximately 5-10 nm), the ratio of 1:6 at a layer thickness of approximately 20-25 nm, for example, and the ratio of 1:10 at a layer thickness of approximately 35-40 nm, for example. In general, therefore, the N/O ratio decreases toward the wire metal body.

Since oxygen is present not in the wire material but only in the layer, the nitrogen intensity of the mixed oxide layer is expressed relative to the oxygen intensity. Thereby the nitrogen content of the mixed oxide layer in the zone of the layer thickness can be characterized indirectly.

AES is a known technique for analysis of the elements of a material present in a near-surface layer. Because of successive ablation of the layer by sputtering, a depth profile of the element distribution in the layer is generated by AES analysis of the respectively exposed layer surface and is used for characterization of the nitrogen content relative to the oxygen content as well as for detection of the concentration profile of the other elements, such as Ni and Ti. The measured intensity of the respective element is obtained in the known way from the Auger electrons emitted by electron bombardment during the AES analysis.

Preferably the nitrogen is present in the mixed oxide layer down to a depth of $2/6$, especially to $3/6$, especially to $4/6$ of the total thickness of the mixed oxide layer, including the first oxide layer. In absolute values, the nitrogen-containing boundary layer extends down to a layer depth of 10 nm, especially 20 nm, especially 30 nm, especially 40 nm, especially 50 nm, for example in a mixed oxide layer with a total thickness of approximately 60 nm. Thereby a hard boundary layer of the mixed oxide layer is generated and the abrasion resistance is improved.

Preferably the wire for production of a wire structure is shaped before the heat treatment, in which case at least one portion, especially several portions of the shaped wire cross over and/or touch one another. The wire structure may comprise, for example, a braid, specifically a braided implant, for example a braided stent, a graft stent, a braded occlusion device or a braided flow diverter. For the braid, meshes bounded by wire crossings are formed in the known way. The braid may be formed from a single wire or from several wires. Conventional braiding techniques may be used for this purpose. In the zone of the wire crossings, the wires or portions may contact one another or be spaced apart from one another.

The wire structure may comprise an intravascular or aneurysm coil. Such coils have one or more spirally wound wires, which touch one another at least in portions and form contact points.

The preferred formation of the wire structure after electropolishing of the wire or in general before the heat treatment for formation of the mixed oxide layer has the advantage that the wire is treated in the straight condition in the solution used for electropolishing, i.e. without wire crossings or contact points. In this way the solution is able to wet the wire surface uniformly in the entire surface zone. Shadowing in the zone of wire crossings and/or contact points is avoided, since the formation of the wire structure takes place only after electropolishing. Because of the uniform ablation achieved thereby during electropolishing, the prerequisite for formation of a homogeneous oxide layer with the most constant thickness possible is created in the subsequent process steps.

Specifically, the oxide layer present after wire manufacture is removed along with impurities by the electropolishing, and so a substantially bright metal surface of the wire remains at first after electropolishing. The wire is removed from the solution and exposed to the ambient air. Because of the contact with air, a natural oxide layer with a thickness of approximately 5 nm forms on the wire surface. This oxide layer is homogeneous and has a substantially constant thickness. It consists mainly of $TiO_2$. The Ni content in the oxide layer decreases rapidly toward the surface, which is substantially nickel-free.

After the wire has been reshaped to a wire structure with at least one crossing, thermal oxidation is carried out in the salt bath. Thereby the surface is modified after electropolishing, and in particular it is passivated and hardened. Since the oxide layer formed naturally after electropolishing is low in nickel or even nickel-free at least in the near-surface boundary zone and thus acts as a barrier to the metal interface of the wire, the thermally formed oxide layer also has only a low Ni content or is low in nickel or even nickel-free, at least in the near-surface boundary zone. By virtue of the subsequent heat treatment in the nitrogen-containing salt bath, a dense mixed oxide layer containing $TiO_2$ is generated on the naturally formed oxide layer. In addition, the mixed oxide layer contains proportions of nitrogen combined as titanium oxynitride and/or titanium nitride. Titanium oxynitride and/or titanium nitride is obtained from the salt bath, for example by using an alkali metal-nitrogen salt, especially potassium nitrate or sodium nitrite, or a mixture of potassium nitrate and sodium nitrite. The thermally formed nitride, especially titanium oxynitride and/or titanium nitride, acts as a hard material, which increases the layer hardness and improves the wear and friction behavior of the functional element, especially an implant.

In contrast to the prior art, electropolishing is therefore carried out at first in this embodiment and is followed by a heat treatment in the salt bath. The net result is that oxidation subsequent to the electrochemical polishing process is achieved by the thermal (inert) salt-bath treatment. Thereby very dense as well as low-friction and wear-resistant oxide layers can be produced, with thicknesses that may exceed 10 nm. Moreover, particularly favorable physical properties, for example with respect to radial force and fatigue behavior, physicochemical properties, especially with respect to nickel release and corrosion behavior, and biological interface characteristics, for example thrombogenicity, of functional elements, especially implants such as stents, can be achieved relatively accurately and simply. Thereby the surface behavior and the biocompatibility can be significantly improved.

The invention is not limited to a special NiTi alloy. To the contrary, it is generally possible to use NiTi alloys, common to medical technology, from which intravascular functional elements, especially implants, the surfaces of which must be protected by an oxide layer, are produced. Examples of alloys are various binary compounds based on Ni, such as, for example, NiTi alloys, especially Nitinol (Ni 55 wt %, Ti 45 wt %), or various ternary compounds, such as, for example, NiTiFe or NiTiNb or NiTiCr, or quaternary alloys such as NiTiCoCr.

The wire may contain at least 5 wt %, preferably at least 10 wt %, preferably at least 20 wt %, preferably at least 40 wt % nickel. The wire may further preferably contain at most 80 wt %, preferably at most 60 wt %, preferably at most 55 wt %, preferably at most 50 wt % nickel. The titanium content may preferably be at least 10 wt %, preferably at least 30 wt %, preferably at least 40 wt %, preferably at least 50 wt %. A surface limit for the titanium content may be 90 wt %, preferably 80 wt %, preferably 65 wt %, preferably 60 wt %, preferably 55 wt %.

Preferably the exposure to heat takes place (at least partly) simultaneously with the immersion in the salt bath, and further preferably exposure to heat takes place at least during 10%, further preferably at least during 30%, even further preferably at least 50%, even further preferably at least 90% of the time of immersion in the salt bath. An additional heat treatment may be carried out before or after immersion in the salt bath. Preferably, however, heat treatment is carried out only during immersion in the salt bath.

In one embodiment, the heat treatment in the salt bath is carried out in at least two steps, wherein the second step is carried out after the introduction of functional means, such as radiologically visible markings, and/or after joining processes. It has been found that, if the mixed oxide layer is damaged by mechanical or thermal joining processes such as the fixation of radiologically visible materials, a second heat treatment is able to anneal out these defects.

The treatment time, especially of the first heat-treatment step, is preferably at least 1 min, preferably at least 2 min and/or preferably at most 8 min, preferably at most 7 min, preferably at most 6 min, preferably at most 5 min, preferably at most 4 min, preferably at most 3 min. The duration of the second heat-treatment step may be at least 50% shorter than the duration of the first heat-treatment step. Preferably the duration of the first heat-treatment step is approximately 2 min to 4 min and the duration of the ensuing second heat-treatment step is approximately 20 s to 60 s.

The upper temperature limit of the heat treatment in the salt bath is preferably 550° C., especially 540° C., especially 530° C., especially 520° C. The lower limit can be 400° C., especially 420° C., especially 440° C., especially 460° C., especially 480° C.

The implant is preferably a braided stent, but may also be a different implant, for example a flow diverter or a stent graft or an intravascular occlusion device or an intravascular coil.

The nickel content in the mixed oxide layer is preferably less than 6 wt %, even more preferably less than 3 wt %, even more preferably less than 2 wt % respectively at least to a layer depth of 30% of the total thickness of the mixed oxide layer, starting from the layer surface, especially to a layer depth of 50% of the total thickness of the mixed oxide layer, starting from the layer surface. Specifically, the low-nickel layer zone may extend to a depth of 20 nm to 40 nm in a layer thickness of 60 nm to 100 nm. The surface of this mixed oxide layer may consist predominantly of $TiO_2$.

A contact angle, i.e. the wetting angle of the surface of the implant when wetted with distilled water, is preferably smaller than 90°, more preferably less than 80°, even more preferably less than 75°, and/or at least 30°, preferably at least 60°. At such a contact angle (wetting angle), the biocompatibility of the implant is relatively high. Further-more, such a contact angle may be adjusted particularly simply by the sequence of manufacturing steps described hereinabove.

In a further embodiment, a salt of the salt bath is an alkali metal-nitrogen salt, preferably a potassium-nitrogen salt and/or sodium-nitrogen salt, especially potassium nitrate and/or sodium nitrite, especially a mixture of potassium nitrate and sodium nitrite. Further salts may (but do not have to) be present. It has been found that a mixed oxide layer, especially containing titanium oxynitride, which is characterized by favorable surface properties (low roughness) and high biocompatibility, can be obtained by such a salt bath containing nitrate and/or nitrite.

It has been found that dense and protective mixed oxide layers are obtained, as shown by the improved corrosion behavior of the implants, when the content of potassium nitrate is greater than the content of sodium nitrite. Specifically, the salt bath may contain the following components:
30-40 wt % $KNO_3$
25-35 wt % $NaNO_2$
rest usual carbon compounds and impurities,
subject to the condition that the content of potassium nitrate is greater than the content of sodium nitrite. The carbon compounds are compounds known to the person skilled in the art in connection with salt baths for heat treatment. Preferably the content of potassium nitrate is 32-38 wt %, especially 34-36 wt %. The content of sodium nitrite may be 26-33 wt %, especially 27-30 wt %.

It is assumed that the high content of $KNO_3$, which has a higher decomposition temperature than $NaNO_2$, favors nitrogen enrichment and oxidation.

The mixed oxide layer may contain at least 10 wt %, more preferably at least 20 wt %, more preferably at least 30 wt %, more preferably at least 40 wt %, more preferably at least 50 wt % titanium oxynitride and/or titanium nitride.

The wire may be an endless wire, which, for example, is wound on a spool or by a spool. Thereby not only is the production method—especially the electropolishing—simplified but also an implant that is easy to handle is obtained.

Preferably a braid is formed from the at least one wire. It is particularly preferred when this braid is formed only after the electropolishing or in general before the heat treatment. In this special embodiment it has been recognized that the crossing points of wire braids (which are known in themselves) usually represent a weakness in the prior art, since the medium for the electropolishing cannot act sufficiently in this zone of overlapping of the wires because of shadowing effects. By the fact that a braid is formed only after the electropolishing, the surface of the wire braid is entirely homogeneous and has relatively good biocompatibility. When the wire is electropolished before braiding, a relatively uniform wire diameter is obtained, thus positively influencing the mechanics of the functional element, especially an implant, and the compliance. If the electropolishing were to be carried out only after braiding, a reduction of the ablation during electropolishing would be suffered in the zone of the wire crossings, where the electropolishing solution is not in sufficiently good contact with the wires. This would lead to irregular wire diameters or uneven development of the surface properties.

In principle, several wires may be braided in order to produce the braid. For example, even a single wire may be used. Other wire structures, for example wound wire structures, are possible.

The above object is achieved independently by an intravascular functional element that can be introduced into a vessel and comprises at least one wire of an alloy containing the alloying elements nickel and titanium, preferably produced by a method according to one of the preceding claims. A mixed oxide layer, which has a layer thickness of 15 nm to 100 nm and which contains $TiO_2$ and at least one nitride, especially titanium nitride and/or titanium oxynitride, is formed on the surface of the wire.

Regarding the advantages of the inventive functional element, reference is made to the advantages explained in connection with the production method.

Preferably the surface layer has a nickel content of less than 6 wt %. Preferably the surface layer has a nickel content of less than 3 wt %, even more preferably of less than 2 wt %.

On the whole, by virtue of the actions described hereinabove, especially the nickel release of implants is minimized, the radial force of medical implants (e.g. of Nitinol) is optimized, the material fatigue behavior of the implant (e.g. of Nitinol) is improved, the corrosion behavior of the implant (e.g. of Nitinol) is improved, the surface roughness of the implant (e.g. of Nitinol) is lessened and the thrombogenicity of medical implants (e.g. of Nitinol) is improved. Moreover, the aggregation of proteins and other blood components, which may lead to thrombosis, is extremely low (by virtue of the low or zero porosity). Instead of braids, it is possible in general to use wire structures having at least one contact point between two wires (devices, for example, that are produced by wire forming or other textile processes).

If a parameter (e.g. the layer thickness) were to vary, the respective maximum value or the (geometric) mean value may be intended.

BRIEF DESCRIPTION OF THE DRAWINGS

The invention will be explained in more detail hereinafter on the basis of exemplary embodiments with reference to the attached schematic drawings, wherein.

DETAILED DESCRIPTION OF THE INVENTION

Figure 1:
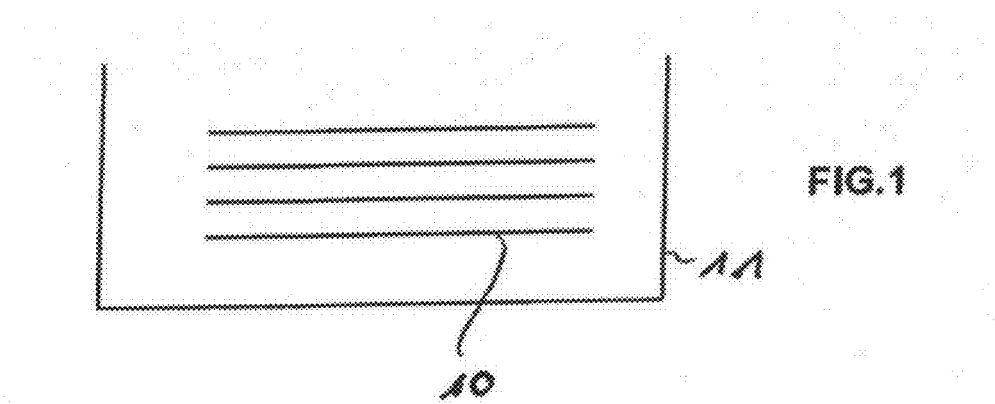
FIG. 1 shows several wires in an electropolishing bath.

FIG. 1 shows a first step for the production of a stent. Several wires 10 (four wires in the schematic drawing) are immersed in an electropolishing bath 11 of an electrolyte. This step may be carried out as in US 2004/0117001 A1, except for the timing sequence.

Figure 2:
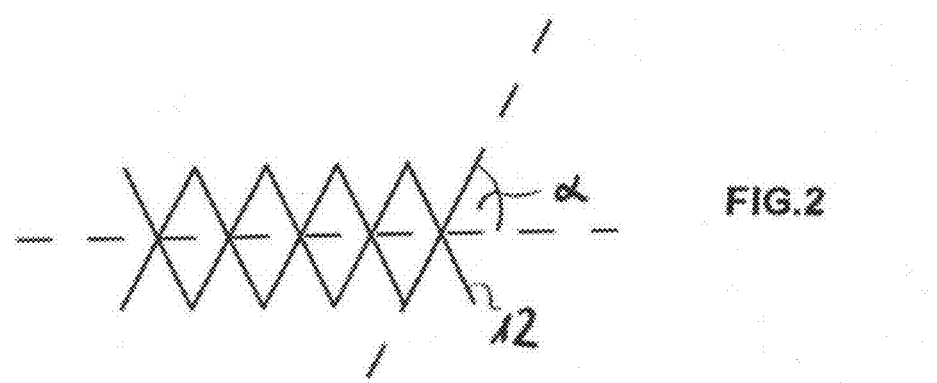
FIG. 2 shows a schematic braid of several wires.
Figure 3:
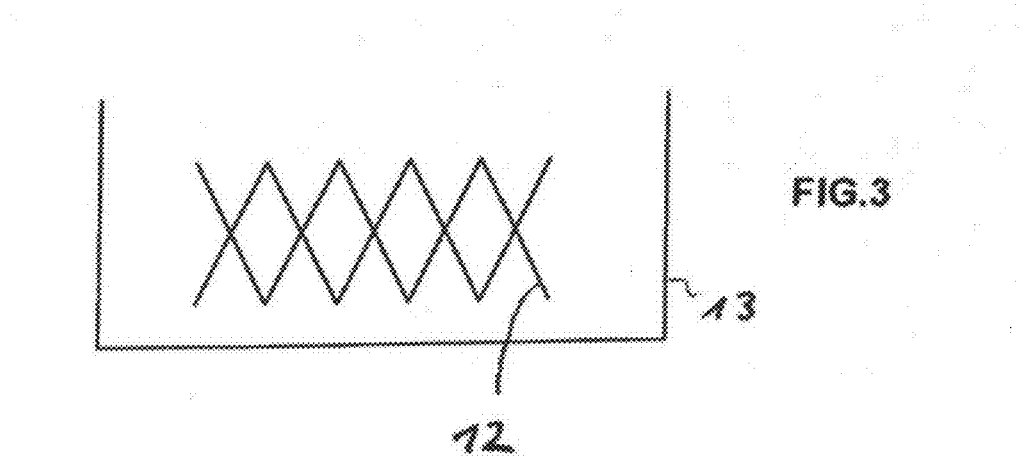
FIG. 3 shows the braid according to FIG. 2 in a salt bath.

FIG. 2 shows (schematically) a braid 12 of wires 10. This braid 12 is illustrated in the expanded condition, so that the entire circumferential surface of the braid 12 is shown in the drawing plane. After the braiding step, braid 12 is immersed and heat-treated in a salt bath 13 (see FIG. 3). In salt bath 13, braid 12 or the stent receives its final structure, including the passivated surface. This does not rule out the possibility that still further processing steps will be carried out.

Example

The invention will be explained by means of an example of a functional element produced from a binary NiTi alloy, such as Nitinol. Other NiTi-containing alloys are possible. In this case the modification of the surface is represented by the thermal treatment in the salt bath, which treatment is responsible for adjusting the nitrogen concentration in the $TiO_2$ mixed oxide layer. The basic component of the functional element, namely the wire, is electropolished in the first step. The electropolishing may be carried out as is usual in the prior art, for example at a temperature T<20° C., using a methanolic sulfuric acid solution. A homogeneous natural oxide layer with a layer thickness of approximately 5 nm is spontaneously formed on the electropolished wire upon contact with the ambient air.

In the second step, a functional element, a stent, is braided using the electropolished wire.

In the third step, the functional element is heat-treated in the salt bath in order to increase the layer thickness. For this purpose there is used a salt-bath composition consisting of the following components:

approximately 35-36 wt % $KNO_3$
approximately 27-29 wt % $NaNO_2$
rest usual carbon compounds and impurities.

It has been found that good results may be achieved when the content of potassium nitrate is greater than the content of sodium nitrite in the salt bath.

The process temperatures are approximately 490° C. to 510° C. In the first treatment step, the functional element is immersed for approximately 2 to 3 minutes in the salt bath. Formation of the oxide layer takes place during this time. The treatment time in the second step is approximately 30 sec or shorter.

Measuring Technique

Figure 4:
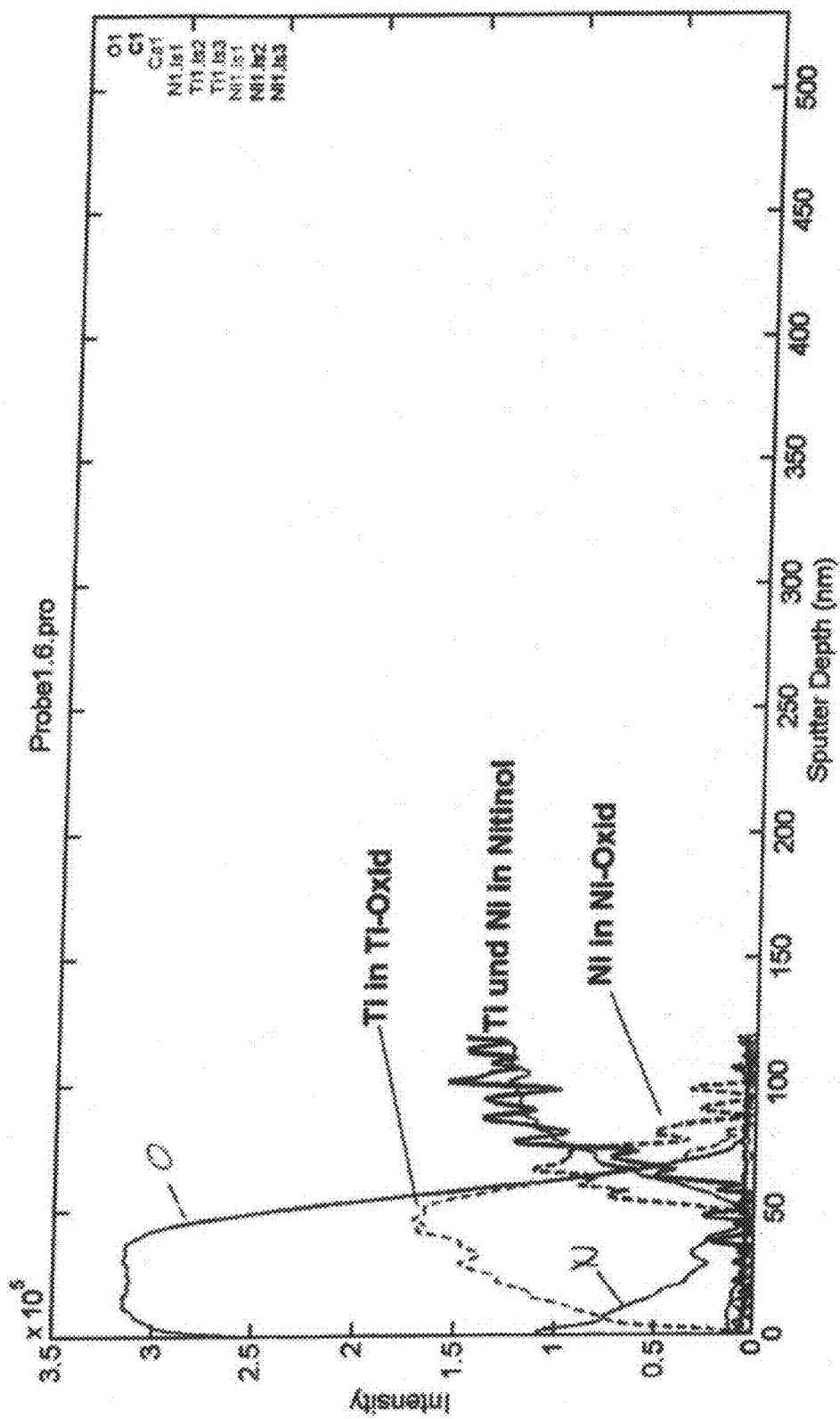
FIG. 4 shows a depth profile of a mixed oxide layer of a functional element according to an inventive exemplary embodiment with a layer thickness of approximately 60 nm (Probe1.6pro)
Figure 5:
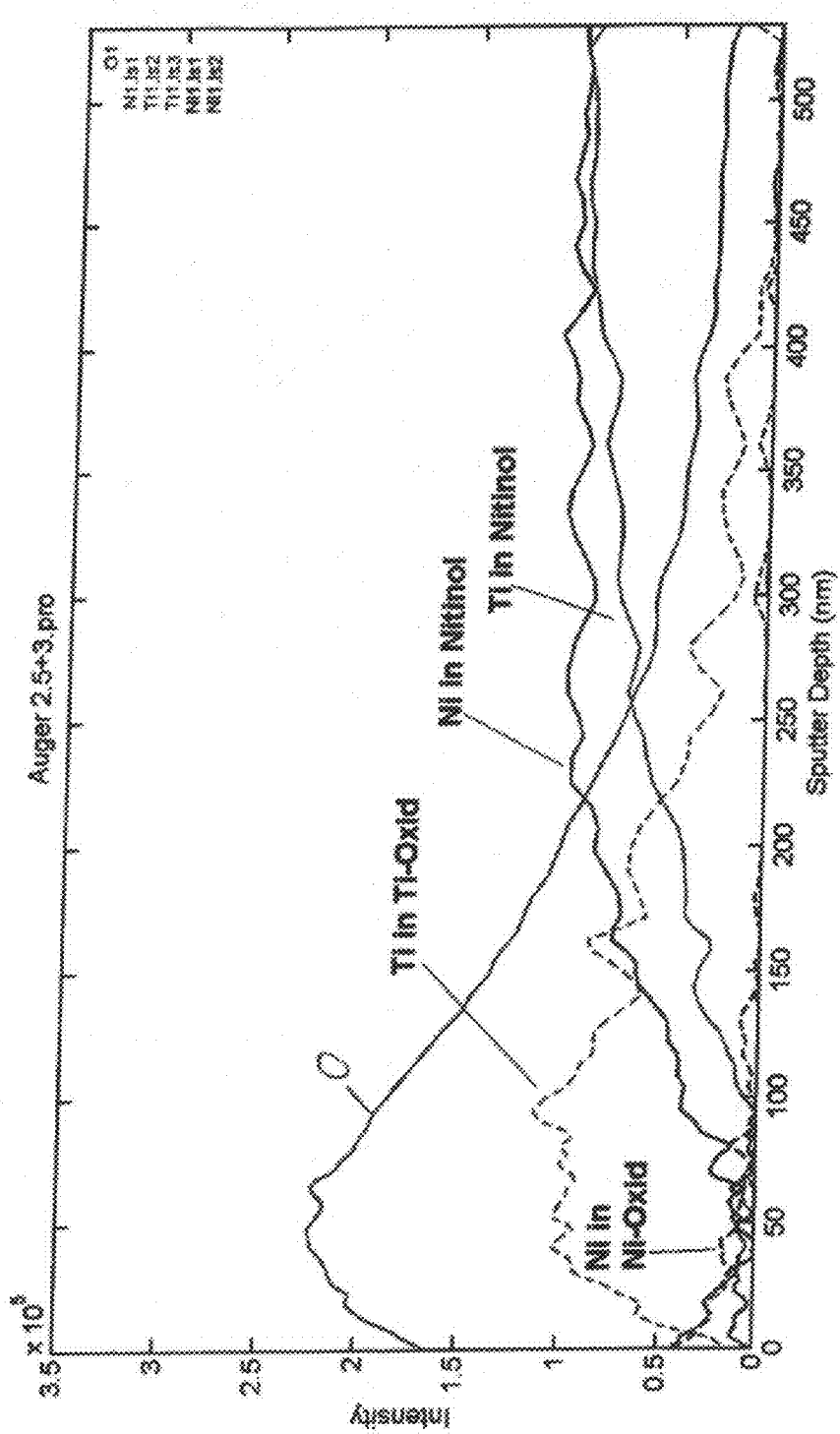
FIG. 5 shows a depth profile of a mixed oxide layer of a functional element according to an comparison example with a layer thickness of approximately 220 nm (Auger2.5+3.pro)

The measurements to determine the AES depth profile according to FIGS. 4 and 5 were made with the following parameters:

Primary electron energy (excitation): 5 keV
Beam current: 20 nA
Electron beam raster (analyzed zone): 20 μm×2 μm
Ion beam energy: 3 keV (FIG. 4, Probe1.6.pro, treated in each case)
Beam current: 2 μA
Ablation rate: 59.3 nm/min
Ion beam raster: 0.8 mm×0.8 mm
Ion beam energy: 1 keV (FIG. 5, Auger2.5+3.pro, untreated)
Beam current: 0.5 μA
Ablation rate: 8.24 nm/min
Ion beam raster: 0.8 mm×0.8 mm
Sample angle (between electron beam and normal to the sample): 30°

The following element peaks were used for determination of the intensities:

Ti1: Ti LMM at 390 eV
Ti2: Ti LMM at 421 eV
N1: N KLL at 389 eV
Ni1: Ni LMM at 849 eV
O1: O KLL at 510 eV

Figure 6:
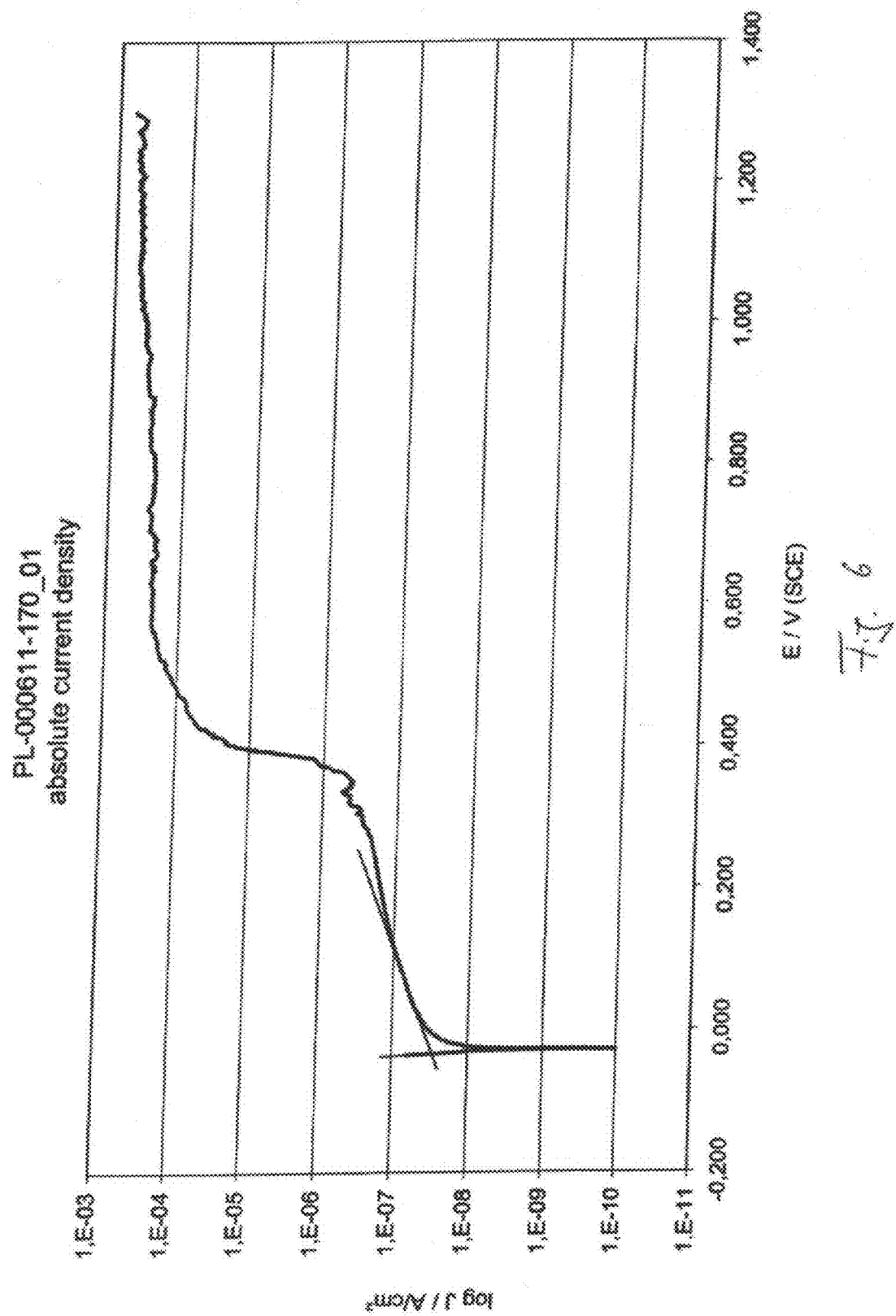
FIG. 6 shows a corrosion curve (0611-170-01) of a functional element as a comparison example, in which a non-electropolished wire is used.
Figure 7:
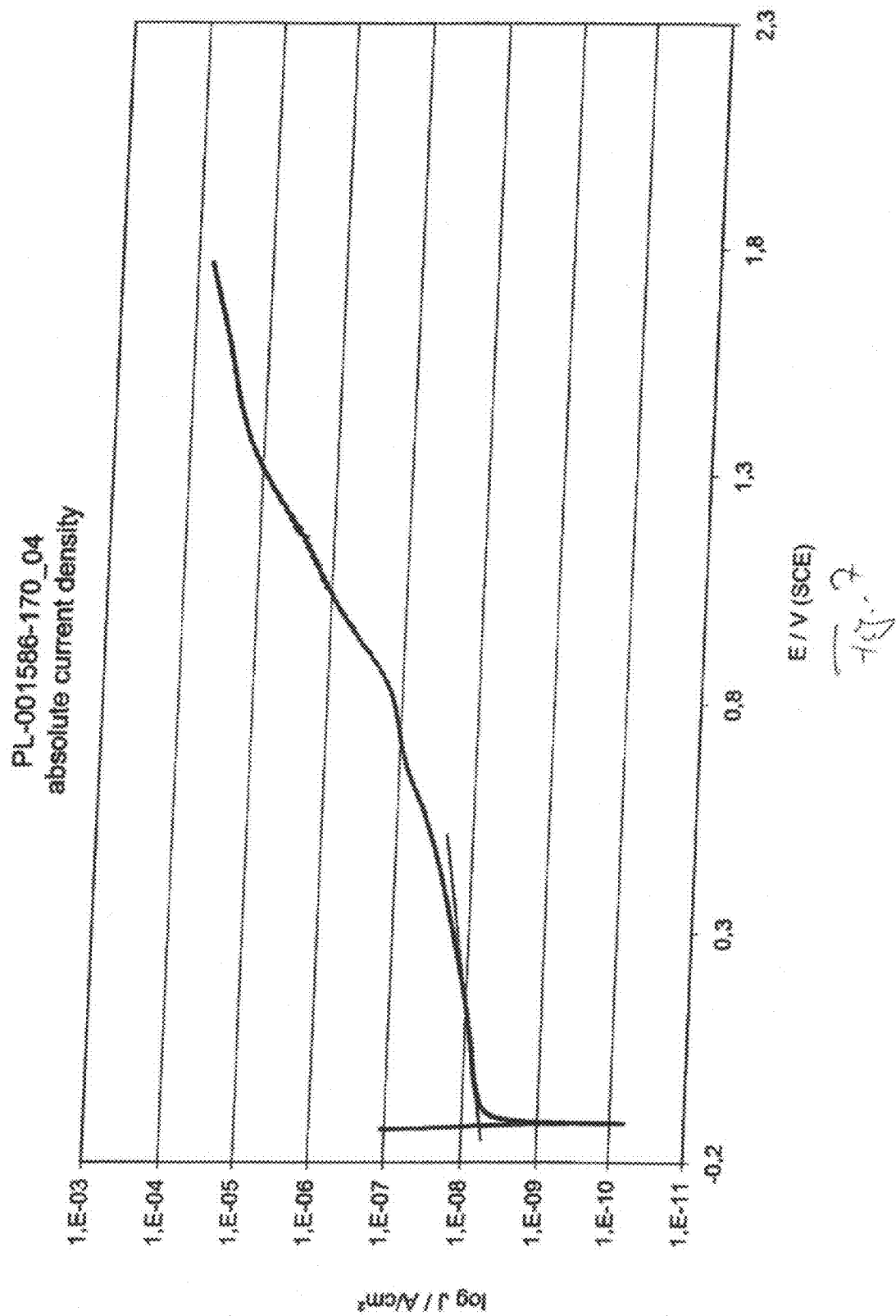
FIG. 7 shows a corrosion curve (1586-170-04) of a functional element according to an inventive exemplary embodiment.

The measurements for the corrosion curves according to FIGS. 6 and 7 were carried out according to ASTM F2129 "Standard Test Method for Conducting Cyclic Potentiodynamic Polarization Measurements to Determine the Corrosion Susceptibility of Small Implant Devices".

Results and Discussion

The depth profile according to FIG. 4, where the sputtering depth is normalized to 500 nm, shows the concentration profile obtained for the layer elements after the process explained in the foregoing has been carried out. In the process, the layer thickness is generally determined from the sputtering parameters. Alternatively to the determination of the layer thickness, 50% of the "peak value" of $TiO_2$ is calculated. Accordingly, the layer has a thickness of approximately 60 nm, which is obtained from the intersection of the oxygen peak and the peak for metallic Ti and Ni. The following peaks are marked in FIG. 4:

Oxygen
Nitrogen
Ti in the titanium oxide
Titanium (metallic titanium)
Ni in the Ni oxide
Ni It is particularly obvious that the oxygen peak has the form of a plateau. The plateau extends over a layer depth between approximately 10 nm and 40 nm. One possible explanation is that the oxygen also combines with nitrogen toward the outer part of the layer and then combines with titanium toward the inner part of the layer. The nitrogen is incorporated as a chemical compound in the layer, and specifically as titanium oxynitride. This follows from the shape of the oxygen signal, which forms a plateau. It may also well be that the nitrogen is additionally present even as titanium nitride. In general, the plateau shape means that the oxygen intensity is zonally constant, especially over a layer depth of at least 10 nm.

In the region of the oxygen plateau, the most obvious ratios N/O of the intensities of nitrogen and oxygen in the layer are approximately 1:3; 1:6; 1:10, where the ratio 1:3 is located in the immediate boundary layer of the outer surface of the layer (approximately 5 nm to 10 nm), the ratio 1:6 at a layer depth of approximately 20 to 25 nm, for example, and the ratio 1:10 at a layer depth of approximately 35 to 40 nm, for example. The ratio at the layer surface is approximately 1:2.5.

From FIG. 4 it is further apparent that a distinct enrichment of Ni oxide is present in the inner part of the layer, in other words close to the metallic wire body. The rest of the layer contains hardly any nickel. In particular, the outer boundary layer is low in nickel. This concentration profile could be imposed by the nitrogen, which may well combine preferentially with oxygen rather than with nickel and thus suppress nickel enrichment in the outer part of the layer.

FIG. 5 shows the depth profile of an untreated sample with an oxide layer thickness of approximately 220 nm (see Ni/O intersection). The investigated oxide layer was formed by the heat treatment during wire manufacture. No treatment was carried out for the sample according to FIG. 5, i.e. the manufacturing-related oxide layer was left on the surface of the wire. FIG. 5 shows that the oxygen profile does not form a plateau. The oxygen intensity increases to approximately 50 nm then decreases. In contrast to the layer according to FIG. 4, moreover, a slight enrichment of nickel oxide is apparent in the near-surface zone of the layer. Enrichment of nickel oxide in the zone of the layer close to the metal body is absent. On the whole, the nitrogen intensity in the layer is significantly lower than in the layer according to FIG. 4.

Figure 10:
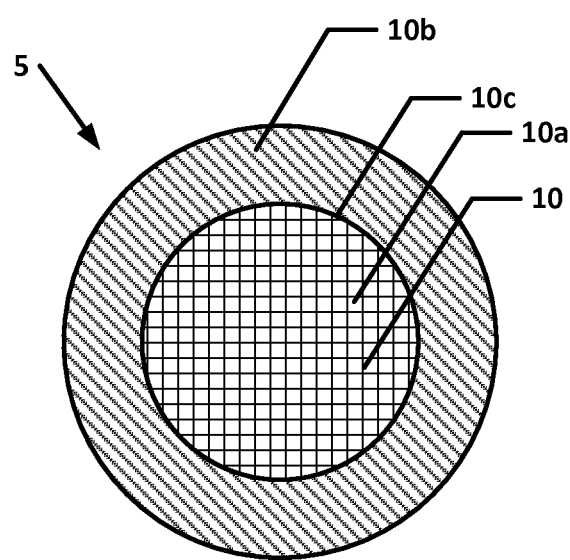
FIG. 10 is a schematic of a portion of an intravascular functional element comprising a wire comprising an alloy of nickel and titanium as alloying elements and a mixed oxide layer formed on the surface of the wire.

FIG. 10 is a schematic of a portion of an intravascular functional element 5 comprising a wire 10 comprising an alloy 10*a* of nickel and titanium as alloying elements and a mixed oxide layer 10*b* formed on the surface 10*c* of the wire 10.

The protective behavior of the layer is assessed on the basis of the corrosion curves according to FIGS. 6 and 7, from which the electrochemical behavior of the layers and therefore the layer properties of interest, such as the release of nickel ions, for example, can be deduced. In FIGS. 6 and 7, the current density J in $A/cm^2$ is plotted against the voltage E in V (SCE).

FIG. 7 shows the corrosion curve (1586-170-04) of an inventively produced layer, which exhibits a very low corrosion current density ($<1\times10^{-8}$ $A/cm^2$). This means that the layer has low permeability for metal ions and therefore exhibits a good protective effect. It is particularly important, as follows from the almost linear increase, that no perforation, i.e. no pitting corrosion occurs. Accordingly the layer properties are excellent.

In contrast to this, as shown in FIG. 6, the corrosion current in the conventionally produced layer is greater than $1\times10^{-7}$ $A/cm^2$. Perforations suggestive of the onset of pitting corrosion, i.e., the formation of small holes, can be observed at approximately 400 mV.

Figure 8:
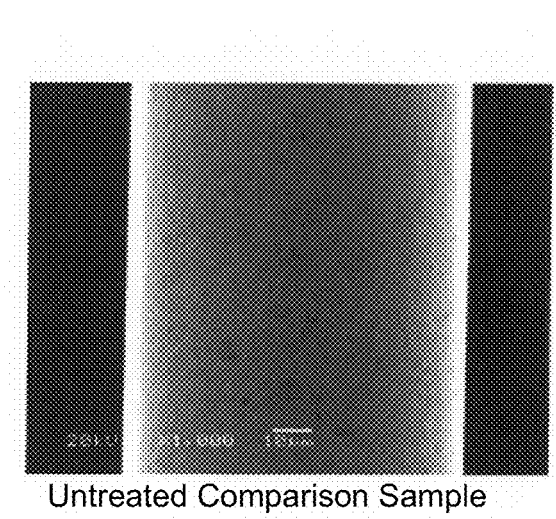
FIG. 8 shows an SEM photograph of an untreated comparison sample.
Figure 9:
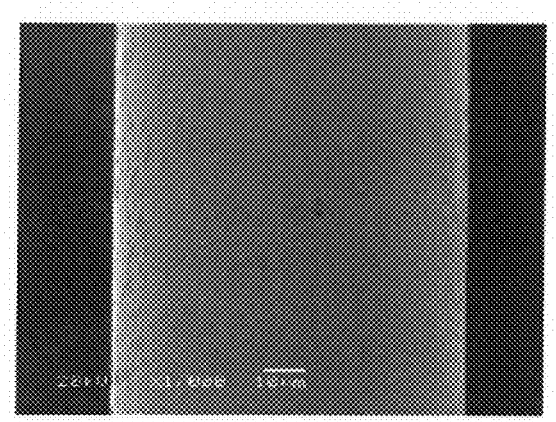
FIG. 9 shows an SEM photograph of a wire surface generated according to an embodiment of the inventive method.

The good surface properties are obvious from the comparison between the surface of an untreated wire having a manufacturing-related oxide layer, illustrated in FIG. 8, and the surface of a wire heat-treated according to the invention, shown in FIG. 9. The oxide layer of the wire according to FIG. 9 is uniformly dense and pore-free.

By means of the inventive method it is possible to produce very corrosion-stable and hard mixed oxide layers, which develop a good protective effect and protect safely against abrasion.

LIST OF REFERENCE SYMBOLS

α Braid angle
5 Intravascular functional element
10 Wire
10*a* Alloy of nickel and titanium as alloying elements
10*b* mixed oxide layer formed on the surface 10*c* of the wire
10*c* surface of the wire
11 Electropolishing bath
12 Braid
13 Salt bath

What is claimed is:

1. A method of manufacturing an intravascular functional element, the intravascular functional element for introduction into a hollow organ;
the intravascular functional element comprising
a wire comprising an alloy of nickel and titanium as alloying elements; and
a mixed oxide layer formed on the surface of the wire, the mixed oxide layer comprising
a layer thickness from 15 nm to 100 nm,
$TiO_2$, and
a nitride, the nitride being a titanium nitride or an titanium oxynitride,
wherein the wire forms a wire structure comprising the wire;
wherein the wire structure comprises a coil for aneurysm treatment or a braid;
wherein the wire structure comprises a contact zone, the contact zone having
a plurality of cross-overs of the wire where the wire crosses-over itself or
a plurality of self-contact points of the wire where the wire contacts itself; and
wherein the mixed oxide layer is homogeneous and has a substantially constant thickness on the wire even at cross-overs or self-contact points;
the method comprising the steps of:
(a) preparing a metal body of the wire;
(b) subsequent to step (a), forming a first oxide layer on the surface of the wire; and
(c) subsequent to step (b), heat treating the wire in a nitrogen-containing salt bath for thermal formation of the mixed oxide layer on the first oxide layer.

2. The method according to claim 1, wherein the layer thickness is at least 55 nm.

3. The method according to claim 1, wherein the layer thickness is at most 95 nm.

4. The method according to claim 1, wherein
a peak of a oxygen concentration in the mixed oxide layer is formed as a plateau.

5. The method according to claim 4, wherein a ratio of intensities between nitrogen and oxygen comprises a range of 1:2.5 to 1:10 in the plateau, and decreases toward an interior of the wire,
wherein the intensities are determined respectively by Auger electron spectroscopy (AES).

6. The method according to claim 1, wherein the nitride extends from an exterior surface of the mixed oxide layer to a depth in the wire of ⅔ of the total thickness of the mixed oxide layer.

7. The method according to claim 1, wherein the mixed oxide layer comprises nickel, the nickel in a region extending from an exterior surface of the mixed oxide layer to a depth of 30% of the total thickness of the mixed oxide layer is at most 6% by weight.

8. The method according to claim 1, further comprising a step of forming an enrichment of nickel oxide in an inner portion of the mixed oxide layer.

9. The method according to claim 1, further comprising a step of forming the contact zone of the wire prior to step (c).

10. The method according to claim 9, wherein the step of forming the contact zone of the wire is performed by braiding the wire.

11. The method according to claim 9, wherein the step of forming the contact zone of the wire is performed by winding the wire into a coil.

12. The method according to claim 1, wherein
a contact angle measured with distilled water is smaller than 90° and at least 30°.

13. The method according to claim 1, wherein
the salt bath comprises an alkali metal-nitrogen salt, a potassium nitrate, a sodium nitrite, or a mixture of potassium nitrate and sodium nitrite.

14. The method according to claim 13, wherein
the content of potassium nitrate is greater than the content of sodium nitrite.

15. A method according to claim 13, wherein
the salt bath comprises
30-40 wt % KNO3
25-35 wt % NaNO2
rest usual carbon compounds and impurities,
wherein a content of potassium nitrate is greater than a content of sodium nitrite.

16. The method according to claim 1, wherein step (c) is performed after performing a step of introducing a functional item, the functional item being a radiologically visible markings, or after performing a step of joining process.

17. The method according to claim 1, wherein step (a) is performed by electro-polishing the wire.

18. An intravascular functional element for introduction into a hollow organ, the intravascular functional element comprises:
- a wire comprising an alloy of nickel and titanium as alloying elements; and
- a mixed oxide layer formed on the surface of the wire, the mixed oxide layer comprising
  - a layer thickness from 15 nm to 100 nm,
  - $TiO_2$, and
  - a nitride, the nitride being a titanium nitride or an titanium oxynitride;
- wherein the wire forms a wire structure comprising the wire;
- wherein the wire structure comprises a coil for aneurysm treatment or a braid;
- wherein the wire structure comprises a contact zone, the contact zone having
  - a plurality of cross-overs of the wire where the wire crosses-over itself or
  - a plurality of self-contact points of the wire where the wire contacts itself; and
- wherein the mixed oxide layer is homogeneous and has a substantially constant thickness on the wire even at cross-overs or self-contact points.

19. A functional element according to claim 18, wherein the mixed oxide layer is disposed in the contact zone.

20. A functional element according to claim 18, wherein the layer thickness is from 15 nm to 60 nm or is from 30 nm to 100 nm.

21. A functional element according to claim 18, wherein the wire structure is non-unitary.

22. A functional element according to claim 18, wherein a peak of a concentration of $TiO_2$ in the mixed oxide layer forms a plateau.

23. A functional element according to claim 22, wherein a ratio of intensities between nitrogen and oxygen comprises a range of 1:2.5 to 1:10 in the plateau, and decreases toward an interior of the wire, wherein the intensities are determined respectively by Auger electron spectroscopy (AES).

24. A functional element according to claim 18, wherein the nitride extends from an exterior surface of the mixed oxide layer to a depth in the wire of ⅔ of the total thickness of the mixed oxide layer.

25. A functional element according to claim 18, wherein the mixed oxide layer comprises nickel, the nickel in a region extending from an exterior surface of the mixed oxide layer to a depth of 30% of the total thickness of the mixed oxide layer is at most 6% by weight.

26. A functional element according to claim 18, wherein an enrichment of nickel oxide is formed in an inner portion of the mixed oxide layer.

27. An intravascular functional element for introduction into a hollow organ, the intravascular functional element comprises:
- a plurality of wires comprising a first wire and a second wire, each wire comprising an alloy of nickel and titanium as alloying elements; and
- a mixed oxide layer formed on the surface of each wire, the mixed oxide layer comprising
  - a layer thickness from 15 nm to 100 nm,
  - $TiO_2$, and
  - a nitride, the nitride being a titanium nitride or an titanium oxynitride;
- wherein the plurality of wires form a non-unitary wire structure;
- wherein the wire structure comprises a coil for aneurysm treatment or a braid;
- wherein the wire structure comprising comprises a contact zone, the contact zone having
  - a plurality of wire cross-overs where the first wire crosses-over the second wire or
  - a plurality of wire self-contact point where the first wire contacts the second wire; and
- wherein the mixed oxide layer is homogeneous and has a substantially constant thickness of each wire even at wire cross-overs or wire self-contact points.

* * * * *